US008698211B2

(12) United States Patent
Toumazou et al.

(10) Patent No.: US 8,698,211 B2
(45) Date of Patent: *Apr. 15, 2014

(54) SENSING APPARATUS AND METHOD

(75) Inventors: Christofer Toumazou, London (GB); Sunil Purushothaman, London (GB)

(73) Assignee: DNA Electronics Ltd., London (GB)

( * ) Notice: Subject to any disclaimer, the term of this patent is extended or adjusted under 35 U.S.C. 154(b) by 135 days.

This patent is subject to a terminal disclaimer.

(21) Appl. No.: 13/352,063

(22) Filed: Jan. 17, 2012

(65) Prior Publication Data

US 2012/0175252 A1    Jul. 12, 2012

Related U.S. Application Data

(63) Continuation of application No. 11/625,844, filed on Jan. 23, 2007, now Pat. No. 8,114,591, which is a continuation-in-part of application No. 10/471,197, filed as application No. PCT/GB02/00965 on Mar. 11, 2002, now Pat. No. 7,686,929.

(30) Foreign Application Priority Data

Mar. 9, 2001    (GB) .................................. 0105831.2

(51) Int. Cl.
*G01N 27/403* (2006.01)
*C12M 1/00* (2006.01)

(52) U.S. Cl.
USPC .................. 257/253; 204/403.01; 204/403.1; 204/416

(58) Field of Classification Search
None
See application file for complete search history.

(56) References Cited

U.S. PATENT DOCUMENTS

| | | | |
|---|---|---|---|
| 4,467,459 A | 8/1984 | Currie | |
| 4,555,623 A | 11/1985 | Bridgewater et al. | |
| 4,777,019 A | 10/1988 | Dandekar | |
| 4,839,000 A | 6/1989 | Eddowes | |
| 5,309,085 A | 5/1994 | Sohn | |
| 5,466,348 A | 11/1995 | Holm-Kennedy | |
| 5,543,024 A | 8/1996 | Hanazato et al. | |
| 5,632,957 A | 5/1997 | Heller et al. | |
| 5,827,482 A | 10/1998 | Shieh et al. | |
| 6,015,714 A | 1/2000 | Baldarelli et al. | |
| 6,060,327 A | 5/2000 | Keen | |
| 6,413,792 B1 | 7/2002 | Sauer et al. | |
| 6,482,639 B2 | 11/2002 | Snow et al. | |
| 6,710,263 B2 | 3/2004 | Kobayashi et al. | |
| 6,953,958 B2 | 10/2005 | Baxter et al. | |
| 7,049,645 B2 | 5/2006 | Sawada et al. | |
| 7,235,389 B2 | 6/2007 | Lim et al. | |
| 7,686,929 B2 | 3/2010 | Toumazou et al. | |
| 7,888,015 B2 | 2/2011 | Toumazou et al. | |
| 8,114,591 B2 | 2/2012 | Toumazou et al. | |
| 2003/0186262 A1 | 10/2003 | Cailloux | |
| 2003/0232354 A1 | 12/2003 | Yu et al. | |
| 2004/0134798 A1 | 7/2004 | Toumazou et al. | |
| 2004/0238379 A1 | 12/2004 | Lindsay et al. | |
| 2004/0262636 A1 | 12/2004 | Yang et al. | |
| 2005/0032075 A1 | 2/2005 | Yaku et al. | |
| 2005/0062093 A1 | 3/2005 | Sawada et al. | |
| 2005/0202504 A1* | 9/2005 | Anderson et al. ................ 435/6 |
| 2008/0032295 A1 | 2/2008 | Toumazou et al. | |
| 2010/0151479 A1 | 6/2010 | Toumazou et al. | |
| 2010/0255595 A1 | 10/2010 | Toumazou et al. | |

FOREIGN PATENT DOCUMENTS

| | | |
|---|---|---|
| EP | 0235024 | 9/1987 |
| JP | 01102352 | 4/1989 |
| JP | 02309241 | 12/1990 |
| WO | 90/13666 | 11/1990 |
| WO | 02/086162 | 10/2002 |

OTHER PUBLICATIONS

Alphey, *DNA Sequencing: From Experimental Method to Bioinformatics*, Bios Scientific Publishers Ltd., Oxford, United Kingdom, pp. i-xiv and 1-25 (1997).
Auroux et al. "Miniaturised nucleic acid analysis" Lab Chip 4:534-546 (2004).
Blazej et al. "Microfabricated bioprocessor for integrated nanoliter-scale Sanger DNA sequencing" Proc. Natl. Acad. Sci. USA, 103:7240-7245 (2006).
Buck "Electrochemistry of ion-selective electrodes" Sensors & Actuators 1:197-260 (1981).
Hanzato et al. "Integrated multi-biosensors based on an ion-sensitive field-effect transistor using photolithographic techniques" IEEE Transactions Electron Devices, 36:1303-1310 (1989).
Iordanov et al. "Sensorized nanoliter reactor chamber for DNA multiplication" IEEE, pp. 229-232 (2004).
Lee et al. "Microchip-based one step DNA extraction and real-time PCR in one chamber for rapid pathogen identification" Lab Chip, 6:886-895 (2006).
Matsuo & Esashi "Methods of ISFET fabrication" Sensors & Actuators 1:77-96 (1981).
Matthews et al., *Biochemistry, 3rd Ed.*, Addison Wesley Longman, Inc. Benjamin/Cummings, pp. i-xxviv, 57-125, and 980-1026 (2000).
Patent Abstracts of Japan No. 095 15:1176 (1991).
Patent Abstracts of Japan No. 342 13:908 (1989).
Purushothaman et al. "Towards fast solid state DNA sequencing" IEEE International Symposium on Circuits and Systems, IV:169-172 (2002).
Purushothaman et al. "Protons and single nucleotide polymorphism detection: a simple use for the ion sensitive field effect transistor" Sensors & Actuators B, 114:964-968 (2006).

(Continued)

*Primary Examiner* — Kenneth R. Horlick
*Assistant Examiner* — David Thomas
(74) *Attorney, Agent, or Firm* — Nixon & Vanderhye PC

(57) ABSTRACT

A method of observing reaction intermediaries during a chemical reaction and comprising detecting an electrical signal output from an ion sensitive field effect transistor exposed to said reaction, and monitoring the detected electrical signal to discriminate discrete fluctuations in the electrical signal, the discrete fluctuations indicating reaction intermediaries occurring during a chemical reaction.

18 Claims, 13 Drawing Sheets

(56) References Cited

OTHER PUBLICATIONS

Shakhov et al. "A sensitive and rapid method for determination of pyophosphate activity" Acta Chem. Scandinavica 36:689-694 (1982).

Sakata & Miyahara "Potentionmetric detection of single nucleotide polymorphism by using a genetic field-effect transistor" ChemBioChem, 6:703-710 (2005).

Sakata & Miyahara "Direct detection of single-base extension reaction using genetic field effect transistor" 3rd IEEE/EMBS Special Topic Conference on Microtechnology in Medicine and Biology, pp. 219-222 (2005).

Sakata et al. "Immobilization of oligonucleotide probes on $Si_3N_4$ surface and its application to genetic field effect transistor" Materials Sci. Eng. C 24:827-832 (2004).

Sakurai et al. "Real-time monitoring of DNA polymerase reactions by a micro ISFET pH sensor" Anal. Chem. 64:1996-1997 (1992).

Shiddiky et al. "Analysis of polymerase chain reaction amplifications through phosphate detection using an enzyme-based microbiosensor in microfludic device" Electrophoresis 27:1-9 (2006).

Shoffner et al. "Chip PCR I. Surface passivation of microfabricated silicon-glass chips for PCR" Nucl. Acids Res. 24:375-379 (1996).

Starodub et al. "Optimisation methods of enzyme integration with transducers for analysis of irreversible inhibitors" Sensors & Actuators B, 58:420-426 (1999).

Sterky et al. "Sequence of genes and genomes" J. Biotechnol. 76:1-31 (2000).

Tabor & Richardson "DNA sequence analysis with a modified bacteriophage T7 DNA polymerase. Effect of pyrophosphorolysis and metal ions" J. Biol. Chem. 265:8322-8328 (1990).

Victorova et al. "New substrates of DNA polymerases" FEBS Lett. 453:6-10 (1999).

Woias et al. "Modelling the short-time response of ISFET sensors" Sensors & Actuators 24-25:211-217 (1995).

Wong & White "A self-contained CMOS integrated pH sensor" Electronic Devices Meeting, pp. 658-661 (1988).

Zhang et al. "PCR microfluidic devices for DNA amplification" Biotechnol. Adv. 24:243-284 (2006).

International Search Report for PCT/GB2002/00965, three pages, mailed Aug. 26, 2003.

Patent Abstracts of Japan, 013:342 (P-908) of JP 01-102352 (1989).

Patent Abstracts of Japan, 015:095 (P-1176) of JP 02-309241 (1991).

Heid et al. "Real time quantitative PCR" Genome Research, 6:986-994 (1996).

Sakata & Miyahara "Direct transduction of allele-specific primer extension into electrical signal using genetic field effect transistor" Biosensors Bioelectronics, 22:1311-1316 (2007).

Tsuruta et al. "Detection of the products of a polymerase chain reaction by an ELISA system based on an ion sensitive field effect transistor" Journal of Immunological Methods, 176:45-52 (1994).

Tsuruta et al. "Quantitation of IL-1β mRNA by a combined method of RT-PCR and an ELISA based on ion sensitive field effect transistor" Journal of Immunological Methods, 180:259-264 (1995).

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: template oligonucleotide

<400> SEQUENCE: 1
acatctgagt ctgtagtcta                                                    20

<210> SEQ ID NO 2
<211> LENGTH: 17
<212> TYPE: DNA
<213> ORGANISM: Artificial Sequence
<220> FEATURE:
<223> OTHER INFORMATION: target DNA

<400> SEQUENCE: 2
ccccaggacg ccccttt                                                       17

<210> SEQ ID NO 3
<211> LENGTH: 10
<212> TYPE: DNA
<213> ORGANISM: Artificial Sequence
<220> FEATURE:
<223> OTHER INFORMATION: probe/primer oligonucleotide

<400> SEQUENCE: 3
aaaggggcgt                                                               10

<210> SEQ ID NO 4
<211> LENGTH: 11
<212> TYPE: DNA
<213> ORGANISM: Artificial Sequence
<220> FEATURE:
<223> OTHER INFORMATION: probe/primer oligonucleotide plus single base
      extension

<400> SEQUENCE: 4 aaagggcgt c                                                              11
```

SENSING APPARATUS AND METHOD

CROSS-REFERENCE TO RELATED APPLICATIONS

The present application is a continuation of application Ser. No. 11/625,844, filed Jan. 23, 2007, now U.S. Pat. No. 8,114,591; which is a continuation-in-part of patent application Ser. No. 10/471,197, filed Mar. 2, 2004, now U.S. Pat. No. 7,686,929; which is the national phase of International Patent Application No. PCT/GB2002/00965, filed Mar. 11, 2002, which claims priority from Patent Application No. GB 0105831.2, filed Mar. 9, 2001; the entire contents of which are hereby incorporated by reference in this application.

FIELD OF THE INVENTION

The present invention relates to a sensing apparatus and method, and particularly though not exclusively to a sensing apparatus and method suitable for DNA sequence determination. More particularly, it relates to use of ion-sensitive field effect transistors (ISFETs) to monitor local fluctuations in ionic charge corresponding with discrete chemical events, especially for example proton release associated with individual nucleotide insertion at the end of an oligonucleotide chain. Monitoring of individual nucleotide insertions by means of a pH sensitive ISFET may be utilised in DNA sequence determination based on conventional Sanger method DNA sequence determination and in identifying allelic variants, e.g. single nucleotide polymorphisms (SNPs), relying on detecting extension of oligonucleotide primers designed to target specific nucleic acid sites.

BACKGROUND OF THE INVENTION

DNA sequencing methods have remained largely unchanged in the last 20 years [Sterky and Lundeberg, 'Sequence analysis of genes and genomes', J. Biotechnology (2000) 76, 1-31]. The Sanger method is a well-known method of DNA sequencing, and comprises DNA synthesis, with termination of DNA replication at points of di-deoxynucleotide insertion. The DNA synthesis is followed by electrophoresis of the synthesised DNA to separate DNA molecules according to their mass to charge ratios, thereby allowing determination of the DNA sequence. A disadvantage of the Sanger method is that electrophoresis is complex, costly and hazardous. It is an object of the present invention to provide a sensing apparatus and method whereby Sanger-type sequence determination employing di-deoxynucletide triphosphates can be carried out without need for separation of extended oligonucleotide strands. However, as indicated above, the invention can he applied more broadly to monitoring of any chemical event which will give rise to a fluctuation in ionic charge, e.g. proton release.

SUMMARY OF THE INVENTION

According to a first aspect of the invention, there is provided a sensing method comprising detecting an electrical signal output from an ion sensitive field effect transistor (ISFET), and monitoring the detected electrical signal to discriminate localised fluctuations of ionic charge, the localised fluctuations of ionic charge occurring at or adjacent the surface of the field effect transistor indicating events occurring during a chemical reaction. More particularly, there is provided a method of observing reaction intermediaries during a chemical reaction and comprising detecting an electrical signal output from an ISFET exposed to said reaction, and monitoring the detected electrical signal to discriminate discrete fluctuations in the electrical signal, the discrete fluctuations indicating reaction intermediaries occurring during a chemical reaction. In a preferred embodiment, said reaction intermediaries arise from one or more nucleotide insertions at the end of a nucleotide chain in a DNA extension reaction (or chain elongation) and individual nucleotide insertions are monitored through detecting change in the measured electrical signal consequent upon proton release with each nucleotide insertion.

The inventors have realised that localised fluctuations of ionic charge which occur at the surface of a field effect transistor ay be measured. Although ion sensitive field effect transistors are already known, they have previously been used to monitor slow changes of for example absolute values of pH in a reaction mixture as a whole. They have not been used to monitor localised fluctuations of ionic charge associated with individual chemical events such as nucleotide addition to a DNA. In known application of an ion sensitive field effect transistor arrangement, a measurement of the absolute value of the pH of the reaction mixture is made every 30 seconds. Typically, many millions of chemical reactions will occur between measurements, and this is seen as a change of the absolute value of the pH. The invention allows individual chemical events to be monitored.

Preferably, the chemical reaction is DNA synthesis, and the fluctuations of ionic charge indicate the insertion of individual di-deoxynucleotide triphosphates (ddNTPs) and deoxynucleotide triphosphates (dNTPs).

A limitation of existing ion sensitive field effect transistor arrangements is that they attempt to measure absolute values of pH and consequently suffer from drift and hysteresis. The invention monitors fluctuations of ionic charge rather than absolute values, and thus avoids this problem.

Preferably, the time at which the fluctuations occur and the magnitude of the fluctuations is monitored to allow sequence determination of DNA.

According to a second aspect of the invention there is provided a sensing apparatus comprising an ion sensitive field effect transistor arranged to generate an electrical output signal in response to localised fluctuations of ionic charge at or adjacent the surface of the transistor, means for detecting an electrical output signal from the ion sensitive field effect transistor, and means for monitoring the detected electrical signal to discriminate localised fluctuations of ionic charge, the localised fluctuations of ionic charge indicating events occurring during a chemical reaction.

Again, preferably, the chemical reaction is DNA extension, and the localised fluctuations of ionic charge indicate the insertion of individual di-deoxynucleotide triphosphates (ddNTP) and deoxynucleotide triphosphates (dNTP). Preferably, the monitoring means is arranged to monitor the time at which the localised fluctuations occur and the magnitude of the localised fluctuations, to allow sequence determination of DNA.

BRIEF DESCRIPTION OF THE DRAWINGS

Specific embodiments of the invention will now be described by way of example only with reference to the accompanying figures, in which.

DETAILED DESCRIPTION

Figure 13:
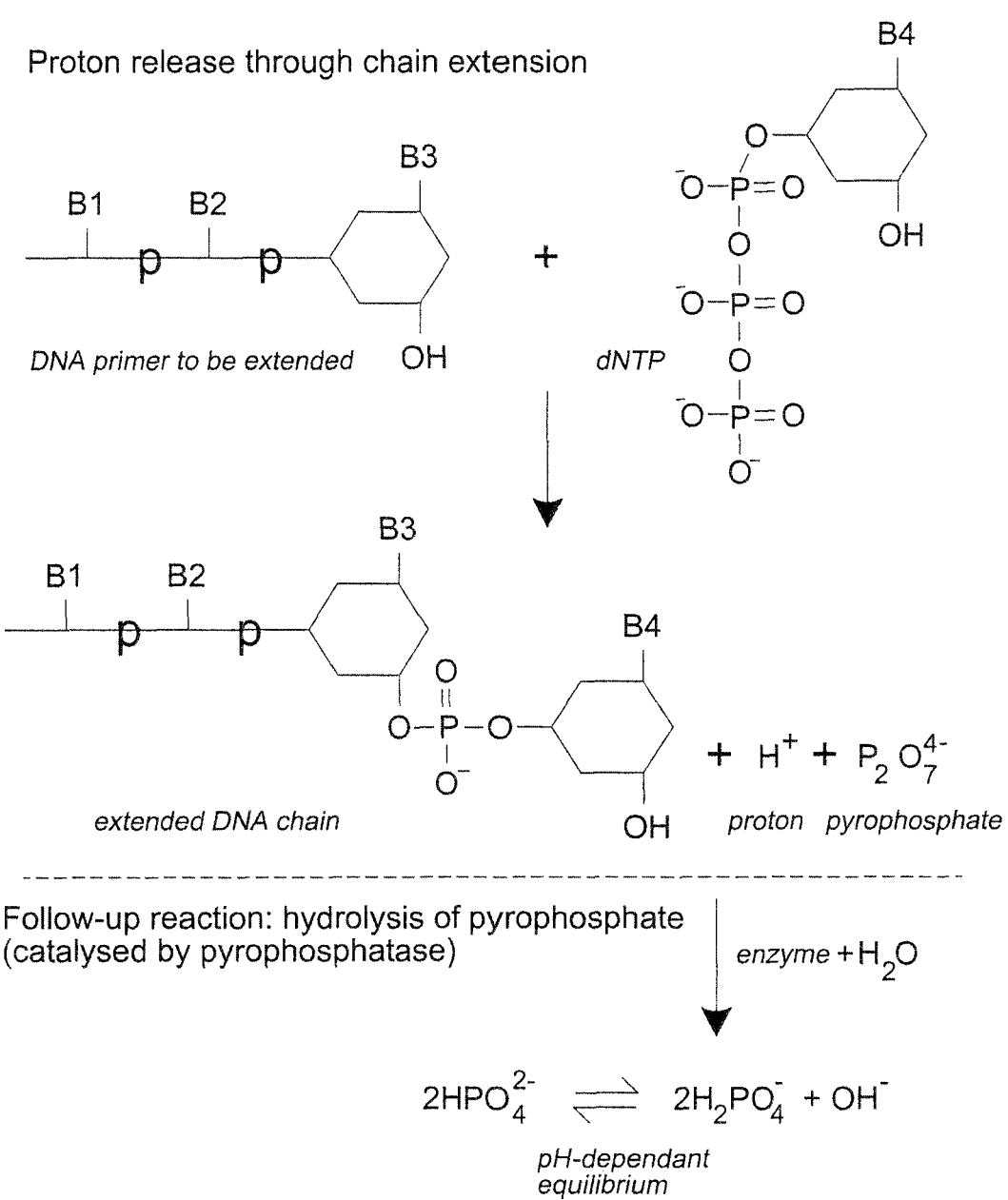
FIG. 13 shows the proton release through DNA extension monitored in applying the invention to DNA sequence determination.

DNA sequencing of the Sanger-type using an embodiment of the invention is performed as follows: A quantity of DNA of interest is amplified using either a polymerase chain reaction or cloning, and the region of interest is primed so that DNA polymerase catalyses DNA synthesis through the incorporation of nucleotide bases in a growing DNA chain thereby releasing hydrogen ions, see FIG. 13. This is accompanied in vivo with the hydrolysis of pyrophosphate, which at physiological pH leads to the consumption of hydrogen ions [Mathews, Holde, Ahern, Biochemistry, 2nd Edn]; see FIG. 13.

Figure 1:
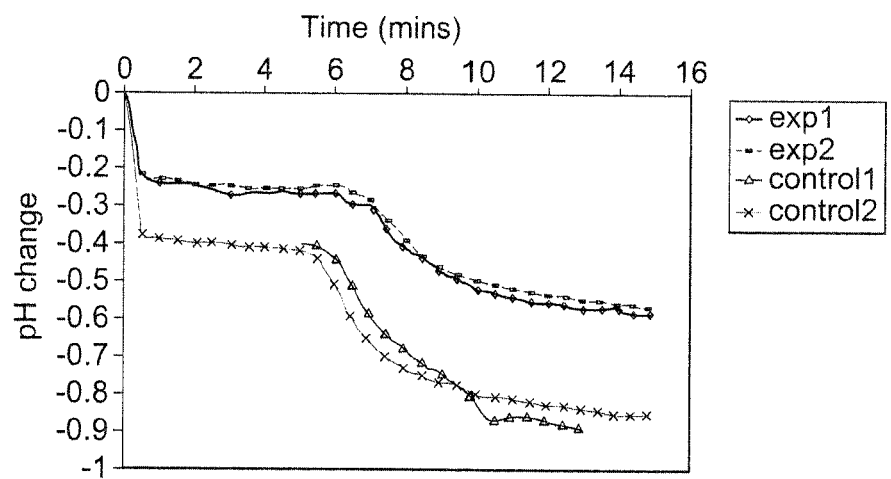
FIG. 1 shows pH changes occurring during pyrophosphate hydrolysis using a buffered reaction medium.

The results shown in FIG. 1 demonstrate the DNA extension reaction and its effect on pH. The pH was measured using a glass electrode arrangement, with measurements of the absolute value of pH taken every 30 seconds. The pH can be seen to fall gradually. The embodiment of the invention uses this reaction to monitor nucleotide insertion, by detecting localised fluctuations of pH which occur at or adjacent the surface of an ion sensitive field effect transistor The ISFET is provided with an ion sensitive silicon nitride layer, on top of which a layer of polymerase is provided. The release of protons from nucleotide insertion during the DNA extension reaction is detected by the ISFET, which may or may not be followed by hydrolysis of pyrophosphate. The magnitude of pH change in either direction (i.e. positive or negative) is detected in order to reliably detect nucleotide insertion, as described below. Individual nucleotide insertion will occur approximately every 3 ms at a temperature of 65° C. [Tabor and Richardson, 'DNA Sequence Analysis with a Modified Bacteriophage T7 DNA polymerase. Effect of pyrophosphorolysis and metal ions', J. Biol. Chem. (1990) 14, 8322-8328.] The ISFET is able to detect rapid pH changes and has an immediate response rate measured to be within 1 ms of a pH change [Woias et al., 'Modelling the short-time response of ISFET sensors', Sensors and Actuators B, 24-25 (1995) 211-217.]

The hydrolysis of pyrophosphate causes either a net consumption or no change of hydrogen ions depending on the pH in which the reaction occurs. In the embodiment of the invention, the reaction is conducted at pH 7. At pH 7 hydrogen ions are overall liberated during nucleotide insertion. The embodiment of the invention thus monitors drops in pH as indicators of nucleotide insertion.

Figure 2:
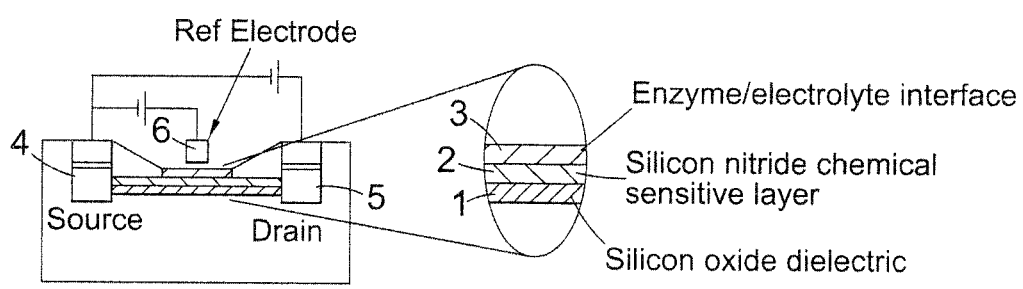
FIG. 2 is a schematic diagram of a field effect transistor which embodies the invention.

A pH sensitive FET which embodies the invention is shown in FIG. 2. The FET is similar to a traditional MOSFET (Metal Oxide Semiconductor Field Effect Transistor). The FET comprises a silicon oxide dielectric layer 1, a silicon nitride chemical sensitive layer 2, and an enzyme/electrolyte interface 3. The layers 1, 2 and interface 3 are located between a source 4 and drain 5 (the conventional configuration of a FET). The FET is provided on a silicon chip, which is encapsulated in epoxy resin to protect it from the reagent mixture. The epoxy resin helps to protect the FET from hydration and charge migration [Matsuo and Esashi, 'Methods of ISFET fabrication', Sensors and Actuators, 1(1981) 77-96.] The FET gate itself is not covered by epoxy resin, so that it may be immersed in the reagent mixture.

The enzyme/electrolyte interface 3 shown in FIG. 2 allows ion sensitivity of the silicon nitride layer 2 to be used for DNA sequencing. The FET functions by producing an exchange of charged ions between the surface of the chemical sensitive layer 2 and the reacting medium (i.e. the enzyme/electrolyte interface 3):

$$SiOH \leftrightarrow SiO^- + H^+$$

$$SiOH_2^+ \leftrightarrow SiOH + H^+$$

$$SiNH_3^+ \leftarrow\rightarrow SiNH_2 + H^+$$

The inclusion of silicon nitride is advantageous because it provides increased and faster sensitivity to changes of pH than would be obtained in the absence of the silicon nitride. In addition the silicon nitride helps to protect the FET from hydration and charge migration.

A non-Nernstian response accounts for the immediate sensitivity of the FET, arising from rapid proton dependant binding and unbinding of charged ions at the insulating gate silicon nitride surface, which results in a reproducible variation in the voltage drop across the silicon nitride layer 2. The variation of the voltage drop across the silicon nitride layer 2 correlates with changes of pH. The voltage drop is monitored using instrumentation circuitry, thereby allowing the detection of individual nucleotide insertions. The measured voltage is referred to as the flatband voltage.

The enzyme/electrolyte interface 3 is deposited on the silicon nitride layer using a known enzyme linkage method [Starodub et al., 'Optimisation methods of enzyme integration with transducers for analysis of irreversible inhibitors', Sensors and Actuators B 58 (1999) 420-426.] The method comprises silanising the silicon nitride layer 2 using aminosilane solution, and then activating the surface using glutaraldehyde. A drop of buffer/polymerase enzyme solution is then deposited on the silicon nitride layer 2 and allowed to dry for about half an hour to form the enzyme layer 3.

The embodiment shown in FIG. 2 uses a reference electrode 6 to provide a measurement of pH changes. The reference electrode is relatively large and difficult to fabricate. An alternative embodiment of the invention does not use a reference electrode, but instead uses a second FET which has the same construction as the first FET, but is provided with a non-enzyme linked layer instead of the enzyme layer 3. This configuration is advantageous because it provides a differential measurement which gives an improved signal to noise ratio.

Figure 3:
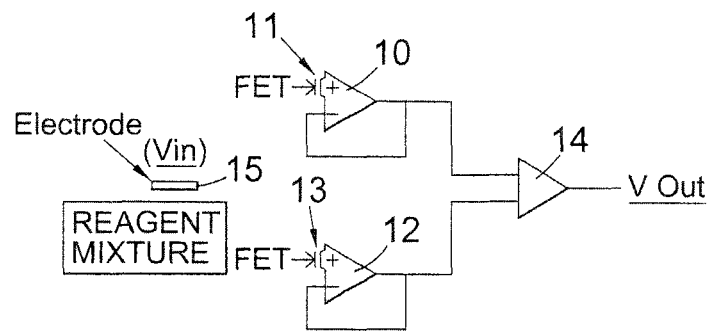
FIG. 3 is a schematic diagram of a pair of field effect transistors which embody the invention.

The alternative embodiment of the invention is illustrated in FIG. 3. The configuration of this embodiment is based upon a known construction [Wong and White, 'A Self-Contained CMOS Integrated pH Sensor', Electron Devices Meeting IEEE 1988] which has previously been used to monitor gradual slow drift of pH. The embodiment comprises a first operational amplifier 10 to which the source of the first FET 11 is connected (the first FET has the enzyme linked layer), and a second operational amplifier 12 to which the source of the second FET 13 is connected (the second FET has no enzyme linked to the FET). The drains of the first and second FETs are connected to a fixed current source (not shown). Outputs from the first and second operational amplifiers are passed to a differential amplifier 14, which amplifies the difference between the outputs to generate an output signal Vout. Negative feedback from the differential amplifier 14 passes to a noble metal electrode 15 which is located in the reagent mixture. The operational amplifier 14 generates an output voltage which keeps the voltage applied to the FETs 11,13 the same despite changes of hydrogen concentration.

The embodiment shown in FIG. 3 is advantageous because it allows rationalisation of fabrication of the FETs 11,13 and the operational amplifiers 10,12, 15.

The FETs 11,13 may be arranged to form the first stage of the operational amplifiers 10,12. This is done for each operational amplifier by replacing a conventional FET of a long tail pair located at the input of the operational amplifier, with the first or second FET 11, 13. This is advantageous because it allows the first and second FETs to form part of the amplification circuitry.

Figure 4:
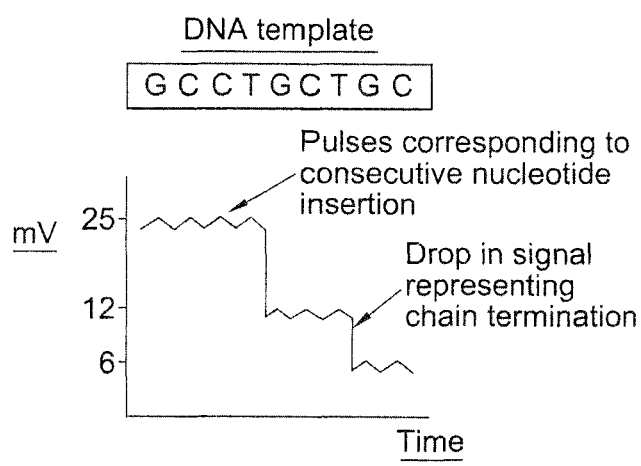
FIG. 4 is a schematic representation of results obtained using the pair of field effect transistors for DNA sequence determination of the Sanger type on a DNA template employing all required dNTPS and a single ddNTP in the reaction mixture.

A schematic example of a flatband voltage detected using the embodiment shown in FIG. 3 is illustrated in FIG. 4. The example is for an NMOS FET with the reaction operating in the ion consumption mode, as described above (the figure would be inverted for a PMOS FET or if the reaction was operating in the ion liberation mode). The flatband voltage consists of pulses representing pH changes associated with nucleotide insertion and drops corresponding to ddNTP insertion and chain termination. The number of local pulses prior to a larger drop determines the number of bases present before termination at a known base; the magnitude of the larger drop is dependant on the ratio of ddNTP:dNTP used in the reagent mixture and is important due to the dependence of read length for that drop. Through repetition of the process four times in different reaction chambers containing each of the four ddNTPS separately, the complete sequence is delineated.

Referring to FIG. 4 in detail, DNA synthesis is performed with termination of DNA synthesis at points of di-deoxynucleotide insertion of thymine bases. Each individual nucleotide insertion causes the liberation of a hydrogen ion, and these are detected as pulses of the flatband voltage, as can be seen in FIG. 4. When the DNA chain reaches a thymine base, nucleotide insertion is prevented for some of the DNA chains, and the amount of hydrogen ion consumption drops leading to a drop in signal output. DNA synthesis continues for those DNA chains which were not terminated at the thymine base, and this is seen as pulses of the flatband voltage at the new lower level. The flatband voltage falls again when the DNA chain reaches a second thymine base (reflecting the fall in available target due to ddNTP addition), and then continues to pulse at the lower level.

The method may be used with or without thermocycling. For example, thermocycling may be used to facilitate optimisation, using tag polymerase as a sequencing enzyme [Alphey, L., 'DNA sequencing: from experimental methods to bioinformatics' BIOS Scientific Publishers, 1997.] The pH of the reagent mixture may be adjusted for example. A decrease of the pH will lead to the production of more hydrogen ions, but will also tend to inhibit the reaction. Trials have shown pH 6.8 to be a useful value of pH. Magnesium may be added to the reagent mixture to actuate the enzyme. The concentrations of the reagents may be modified. A typical thermocycling sequence is set out in Table 1.

TABLE 1

| Cycle Sequencing | | |
|---|---|---|
| Temperature | Duration | Function |
| 95° C. | 30 sec | Denaturing of DNA template |
| 55° C. | 30 sec | Annealing of primer |
| 72° C. | 60 sec | DNA extension and termination |

Operating within a thermal cycler enables multiple repetition of the sequencing process with minimal manipulation. This allows signal to noise boosting and easier delineation of difficult to read regions such as GC rich regions or areas of single nucleotide repeats.

Recombinant T7 polymerase may be used instead of taq polymerase. Where T7 polymerase is used, this may provide increased speed and improved accuracy of monitoring nucleotide insertion.

The steps used to fabricate the ion sensitive FET are set out below:
PURIFIED SILICON SUBSTRATE
ADDITION OF DOPANT: PRODUCTION OF p-TYPE SUBSTRATE
SURFACE OXIDATION: $SiO_2$ LAYER GENERATION
SOURCE/DRAIN DEFINITION AND IMPLANTATION
SILICON NITRIDE DEPOSITION USING LPCVD*
CONTACT FORMATION
PASSIVATION
*Low Pressure Chemical Vapour Deposition The FETs and in particular those shown in FIG. 3, and the amplification stages may be replaced or combined with PMOS transistors.

The length of DNA that can be sequenced will normally be limited by the signal to noise at distal bases as the signal decays with ddNTP insertion. Using PMOS FETs should allow extension of the read length, but may involve a possible compromise over the location of more proximal bases. Installation of two separate FET circuits, of the type shown in FIG. 3, one NMOS pair of FETs and one PMOS pair of FETs should provide the optimum read length. Biasing in weak inversion is possible, since the measurement to be made is of changes to output, rather than absolute values, and absolute linearity in signal amplification for signal analysis is not required.

Measurements may be repeated to provide improved signal to noise ratios.

Since pH sensitive ISFET sensing apparatus can be employed in accordance with the invention to detect individual nucleotide insertion at the 3' end of an oligonucleotide chain, DNA sequencing in accordance with the invention extends to embodiments in which single nucleotide extension is monitored, e.g. such extension of a primer on a template to identify single nucleotide polymorphisms (SNPs) in amplified genomic sequences. SNPs are receiving considerable interest due to the fact that many have now been linked to propensity for various diseases and drug efficacy. SNP detection is thus of interest for disease diagnosis, screening and personalised drug therapy. A SNP is defined as variation at a single base position generally affecting at least 1% of a defined population. Such a variant may be a substitution, insertion or deletion. Although SNPs do not necessarily cause disease, their association with disease and with effects on the pharmokinetics of many drugs provides information for diagnosis and pharmacological treatment options for many different diseases. There are currently over 1.8 million identified SNPse.

For the purpose of detection of SNPs, oligonucleotide primers may be employed of length n designed to hybridise to a target DNA whereby occurrence of a particular nucleotide at position n+1 in the target, a position of allelic variation, can be detected by providing complementary nucleotide for that position (either a dNTP or ddNTP) under conditions permitting extension of the primer by DNA polymerase. Such extension performed at or close to the surface of an ISFET operating in accordance with the invention may be observed as a change in signal associated with proton release consequent upon nucleotide insertion.

Where a SNP needs to be determined, e.g. the type of nucleotide substitution, then four separate reaction mixtures may be presented to the sensing apparatus each containing template strands incorporating the SNP, but each providing a different possible nucleotide for insertion (A, T, C or G). Such SNP identification is illustrated by FIGS. 6 to 10.

Figure 6:
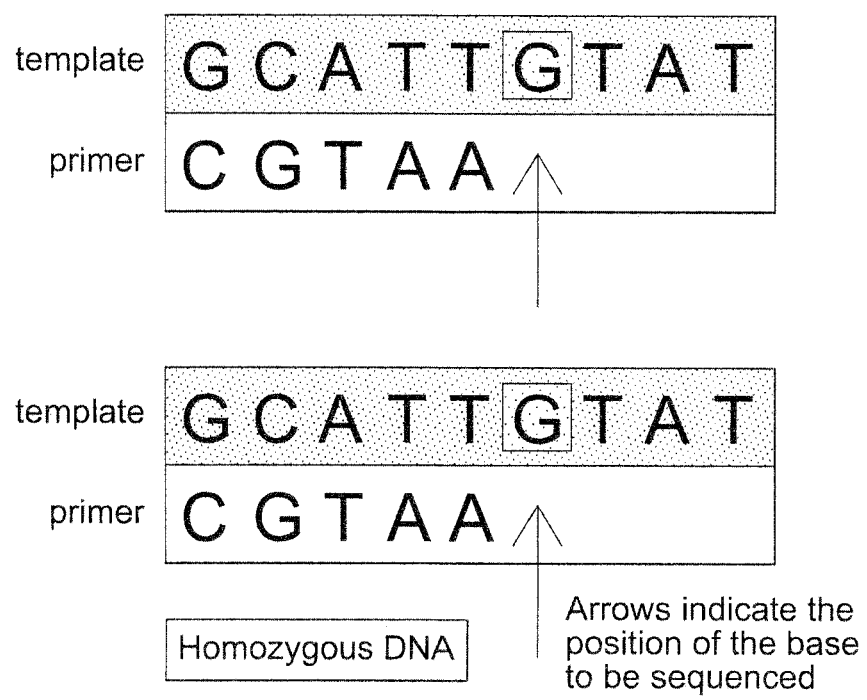
FIG. 6 shows DNA templates and primers employed to illustrate use of a sensing apparatus of the invention for homozygous SNP detection.
Figure 8:
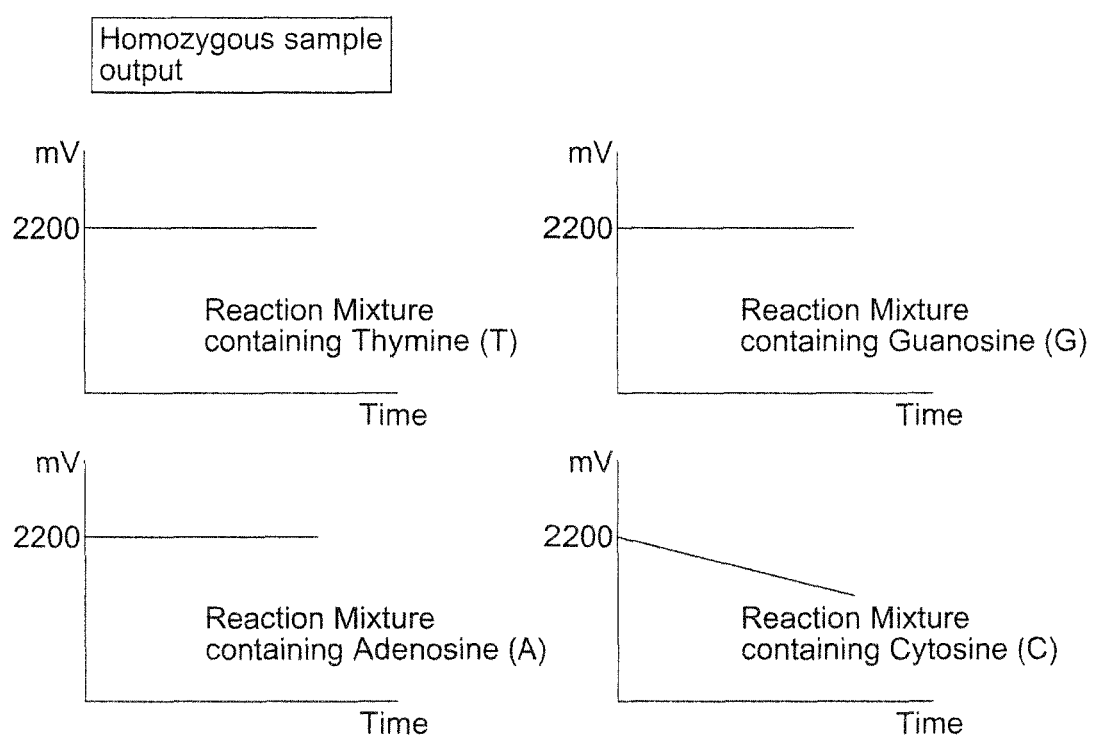
FIG. 8 shows the signals observed with modelling of homzyogous SNP detection using the templates and primers set out in FIG. 6.

FIGS. 6 and 8 illustrate determination of a homozygous SNP by single nucleotide primer extension where all template strands derived from a region of genomic DNA, e.g. by nucleic acid amplification, incorporate the same SNP substitution. In this case, only one reaction mixture is observed to cause pH drop associated with proton release detectable by the ISFET. Four reaction mixtures were employed each containing a different dNTP (dTTP, dGTP, dATP or dCTP). Only the reaction mixture providing cytosine (C) produced a signal drop corresponding with single nucleotide extension of primer indicating that the nucleotide at the pre-primed position on both DNA template strands is the nucleotide complementary to C, namely guanosine (G).

Figure 7:
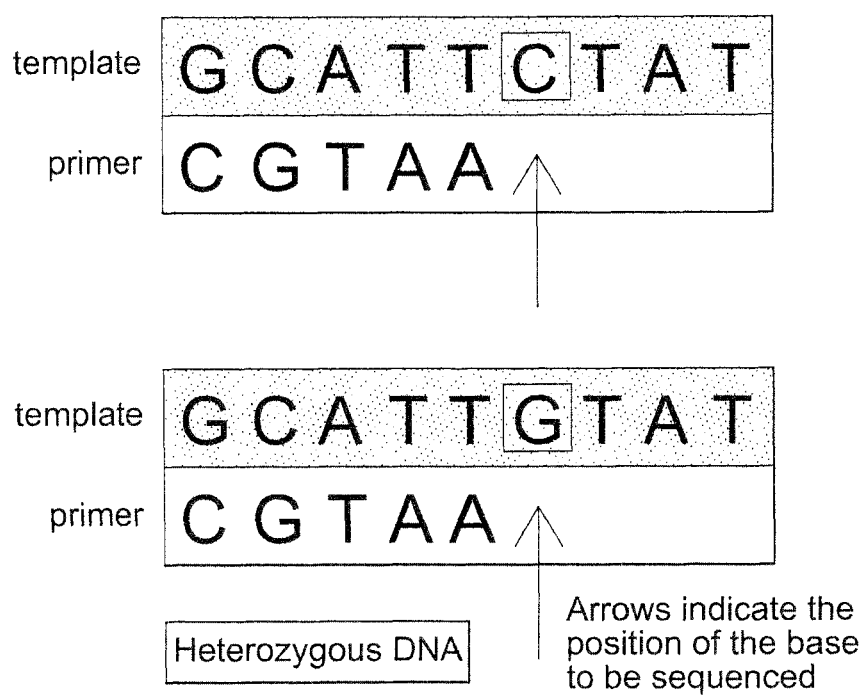
FIG. 7 shows DNA templates and primers employed to illustrate use of sensing apparatus of the invention for heterozygous SNP detection.
Figure 9:
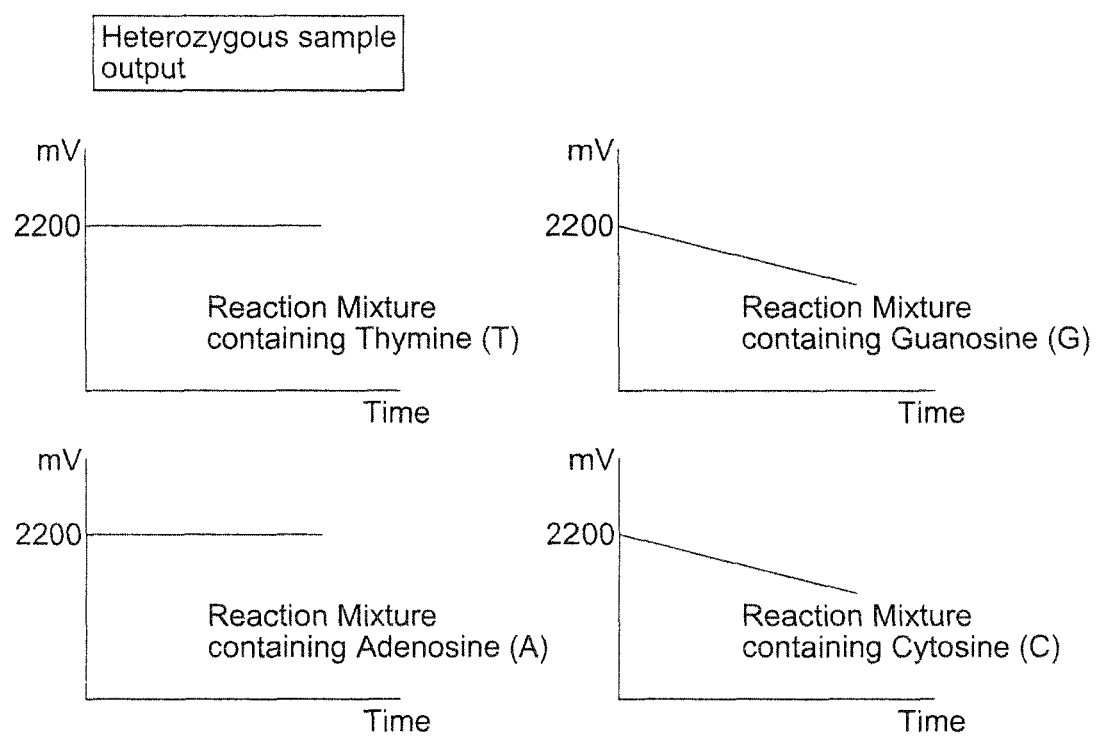
FIG. 9 shows the signals observed with modelling heterozygous SNP detection using the templates and primers set out in FIG. 7.

Individuals may possess a 50:50 mix of two bases at a particular DNA site, i.e. be heterozygous at the position. FIGS. 7 and 9 illustrate determination of an heterozygous SNP employing an ISFET in accordance with the invention where two different bases are present at the relevant genomic position and are identified by monitoring single nucleotide primer extension on corresponding template strands in separate reaction mixtures each containing a different dNTP. Again four reaction mixtures were employed each containing a different dNTP. Two reaction mixtures produced a pH drop corresponding with single nucleotide extension by insertion of different nucleotides to each primer. These were the reaction mixtures providing cytosine and guanosine indicating the presence of their complementary counterparts at the pre-primed positions of the DNA template strands. If the magnitude of the drops are compared, the two drops are roughly equal and the sum of the drops roughly equal to that seen with modelling of homozygous SNP detection.

Figure 10:
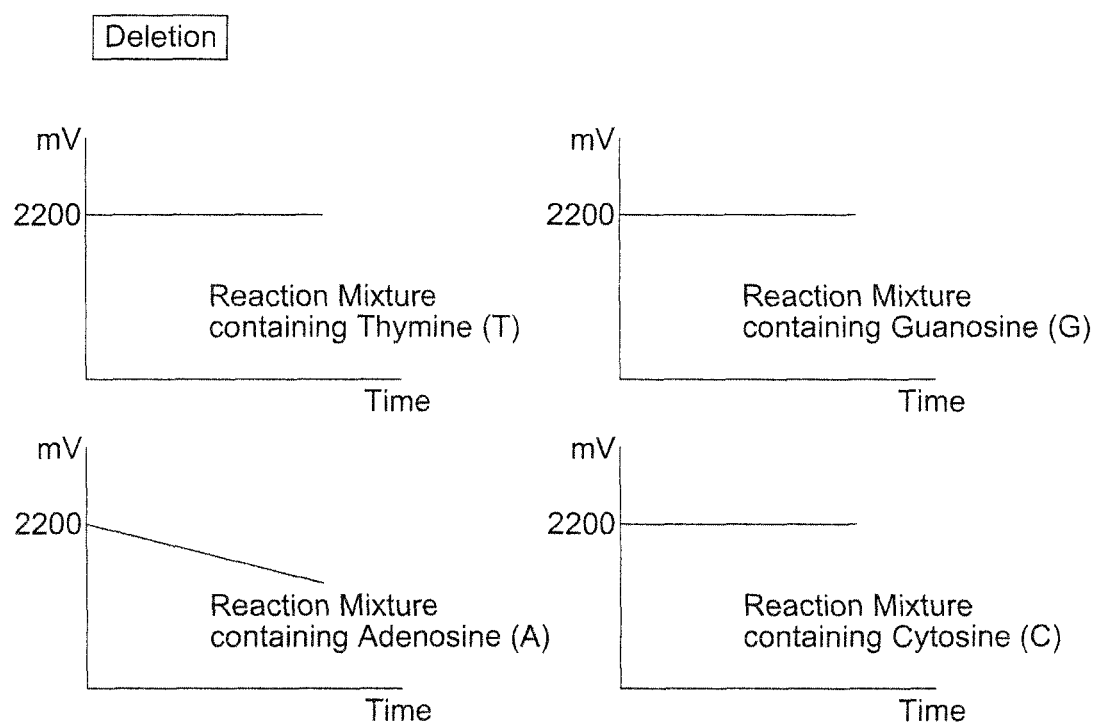
FIG. 10 shows signals observed in detecting a nucleotide deletion as an allelic variant in a DNA sequence.

Such monitoring of primer extension may similarly be employed to identify a deletion allelic variant as illustrated by FIG. 10, or an insertion allelic variant. With reference to the signal outputs of FIG. 10 used to identify a deletion, again an oligonucleotide primer was employed of length n to target a defined position in target DNA at which the deletion occurs (position n+1 in the complementary target strand with hybridised primer). Four reaction mixtures were provided containing primer, DNA template incorporating the deletion, and one of each of the four dNTPs. An ISFET output drop occurred in the chamber providing adenine (A) indicating the base thymine (T) to be present at the first nucleotide position in the template after the 3' end of the primer. It was possible to deduce that this accorded with a deletion by reference to comparative sequence information.

Detection of allelic variants in amplified target regions of genomic DNA may also be achieved by using an oligonucleotide probe specific for the variant of interest such that it hybridises to the target DNA at the site of the variant if present. Such allele specific hybridisation may also be identified by detecting single base extension of the probe by ISFET monitoring of consequent proton release. Such allele specific hybridisation may be utilised in determining both point and more extensive mutations, e.g. deletions of more than one base pair, for disease diagnosis.

For ISFET monitoring of single base extension of a primer or variant specific probe, e.g. for determination in amplified DNA of a disease-linked variant allele, the ISFET will be presented to the reaction mixture for DNA hybridisation and extension in a low volume, e.g. 50 µl or less, chamber or well, e.g. provided in a polydimethylsiloxane (PDMS) plate. Such apparatus is illustrated in FIG. 5 and exemplification of use of such apparatus for single base extension monitoring is given in Example 1 below.

Figure 5:
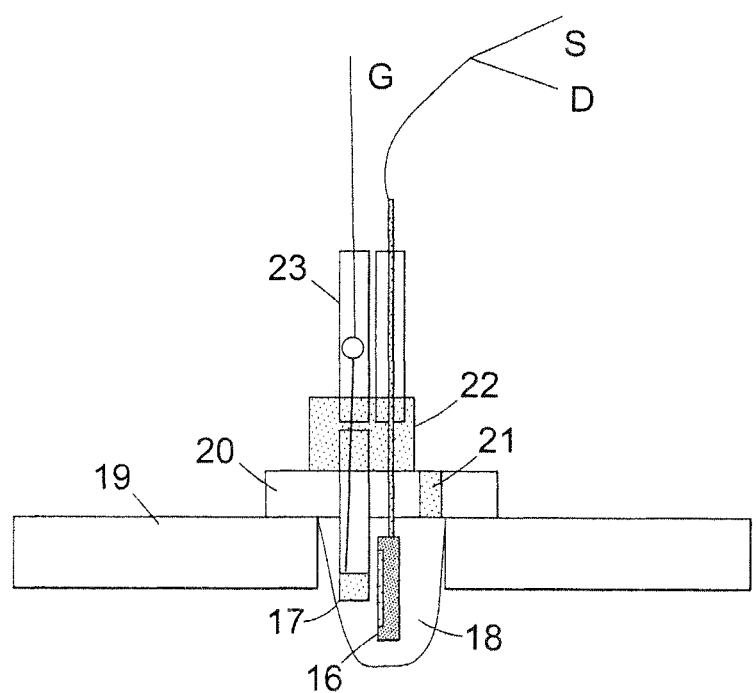
FIG. 5 illustrates ISFET sensing apparatus suitable for example for single base extension monitoring, e.g. such monitoring for SNP detection.

With reference to FIG. 5, the ISFET (16) and a silver/silver chloride reference electrode (17) are both provided in a low-reaction volume chamber (18) in a polydimethylsiloxane (PDMS) plate (19) with the reaction chamber having a covering (20) of PDMS in which is provided an inlet (21) for reagent addition. Above the covering is a seal (22) through which connections to instrumentation run protected by tubing (23) connecting with gate (G), source (S) and drain (D) terminals of the ISFET. The output of the ISFET was measured using constant charge source-follower instrumentation which monitored pH by keeping the ISFET gate voltage and drain current constant and recording changes in gate-source voltage, corresponding to the pH-dependent change in the ISFET's flatband voltage. By placing the ISFET in a thermostated waterbath, single nucleotide extension of an oligonucleotide primer on a DNA target may be monitored at 37° C. or close to 37° C.

The low volume reaction chamber housing the ISFET may be a microfluidic chamber of a microfluidic device or cartridge. Incorporation of an ISFET into a PDMS microfluidic chamber may be achieved by curing the PDMS with the ISFET at 60° C. or less for no more than 4 hours. The desired microfluidic chamber may then be created around the IFSET, e.g. by manually removing PDMS in the region of the IFSET sensing region. The ISFET may be embedded in a horizontal plane at the bottom of a low volume reaction chamber, which is provided with microchannels for sample delivery. Such a device is shown schematically in FIG. 11 with the ISFET (24) embedded in the base (25) of a low reaction volume chamber (26) of less than one nl (typical dimensions 100 µm×100 µm×10 µm). A number of such ISFET-containing chambers may be provided in a single microfluidic chip. Means may be provided whereby target DNA of a single sample may be delivered to more than one such chamber for simultaneous testing for more than one variation. The ISFET, housed in a microfluidic chamber, may be an integral part of a chip such as a silicon chip with resistive on-chip heating elements and temperature sensors to control the temperature for DNA hybridisation and extension. For monitoring of single base primer/probe extension, the temperature of the reaction mixture will desirably be maintained constant at the optimal temperature for the DNA polymerase and thereby DNA extension.

Where the DNA sample is liable to contain both target DNA and unwanted background DNA, immobilisation of DNA probe or primer capable of hybridising to the target is required to separate target DNA from background DNA. For this purpose, the DNA primer or probe for DNA extension monitoring may be immobilised on beads which are brought into the vicinity of the ISFET sensing surface or linked to the ISFET directly or indirectly. In either case, immobilisation of the probe or primer will be such as to enable the required separation step for target DNA with washing to remove unwanted DNA. Ensuring close proximity of the DNA probe or primer to the ISFET sensing surface by such immobilisation also has the benefit of increasing signal to noise ratio by localising the pH changes caused by the chain extension reaction close to that surface.

Figure 11:
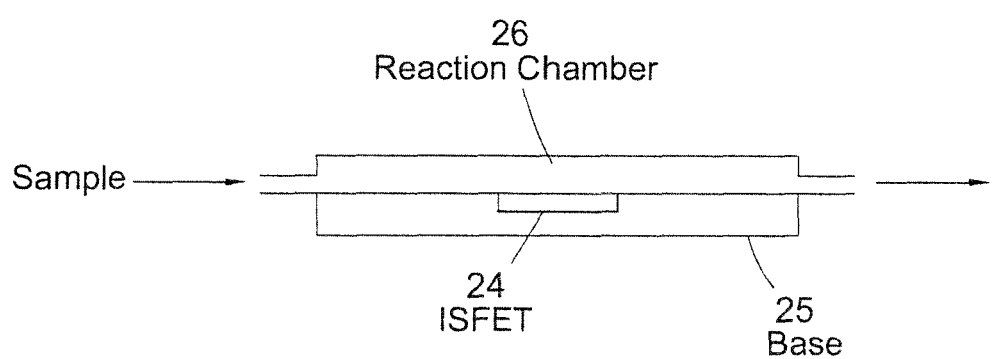
FIG. 11 is a schematic diagram of a microfluidic device containing an embedded ISFET in a low volume reaction chamber as may be employed in detecting DNA extension, including single base primer extension.
Figure 12:
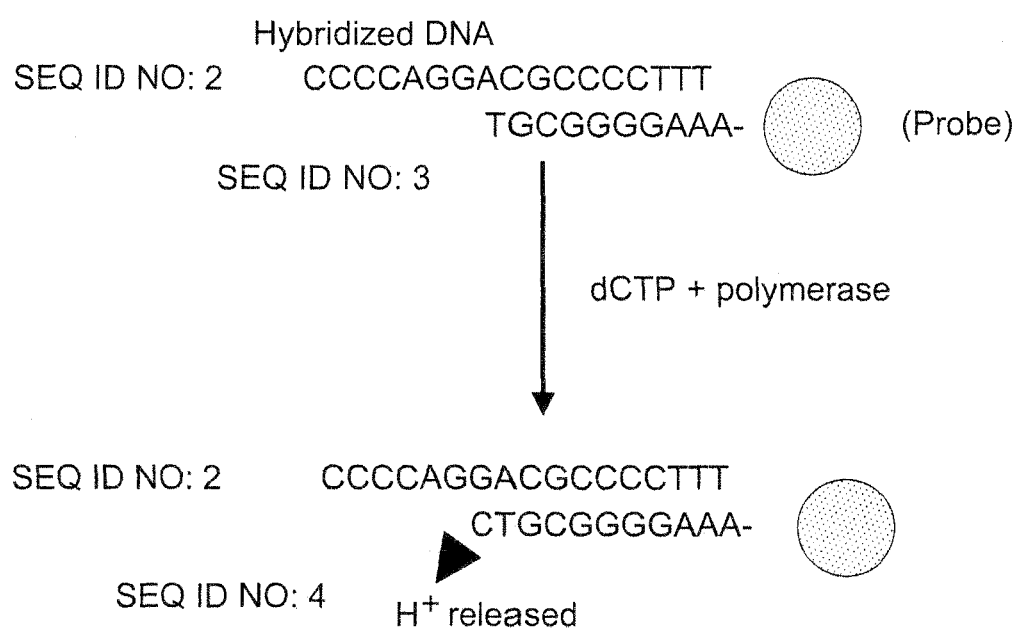
FIG. 12 illustrates single base primer extension on a bead as may be monitored using a device as shown in FIG. 11.

Thus, DNA extension monitoring in accordance with the invention may preferably be of DNA primer or probe extension occurring on beads as illustrated by FIG. 12. The oligonucleotide primer or probe is immobilized on the beads such that it will hybridise and thereby capture target DNA in the reaction chamber. If a dNTP complementary to the target template strand immediately after the 3' end of the primer is provided in the reaction mixture under DNA extension conditions, then a change in the ISFET output will be observed indicative of proton release as result of nucleotide addition to the primer. Use of beads may be advantageously combined with use of an ISFET lying in a horizontal plane at the bottom of the reaction chamber as shown in FIG. 11 such that the beads settle in the vicinity of the ISFET sensing surface. The beads may be chosen such that gravitational settlement alone brings the beads into the vicinity of the ISFET sensing surface. Alternatively, magnetic/metallic beads may be employed and magnetically drawn into the vicinity of the ISFET sensing surface. The beads may be spherical particles synthesised from any suitable material for the attachment of DNA, e.g. silica, polystyrene, agarose or dextran. The size of the beads may be adjusted to assist gravitational settling. The beads can be washed off the sensor surface using water or buffer solution. Linkage of DNA primer or probe to the beads may be achieved using conventional methods, e.g. functionalisation of the bead surface. A spacer may be employed. The coverage of the bead is controlled by adjusting the DNA to bead ratio. For example silica beads (e.g. about 200 nm diameter) may be employed and DNA directly immobilized on the beads or immobilized following modification of the beads to provide a carboxylic functional group. Plastic beads (e.g. plastic microbeads of about 1 μm) may for example alternatively conveniently be employed.

As an alternative to the use of beads, as indicated above DNA primer or probe for capture of target DNA may be linked directly or indirectly to the ISFET whereby nucleotide extension is detected by the ISFET sensing surface in the presence of target DNA. Provision of DNA primer or probe immobilised on the ISFET may employ techniques well known for DNA probe immobilisation on a solid surface, e.g. such techniques well known from the DNA microarray art. Thus, DNA probe or primer immobilisation on the ISFET may be achieved by in situ-oligonucleotide synthesis (by lithography or other means).

The following references provide additional background information relevant to the invention:

Shakhov and Nyrén, 'A Sensitive and Rapid Method for Determination of Pyophosphate Activity', Acta Chem. Scand. B 36 (1982) 689-694;

R. Buck, 'Electrochemistry of Ion-Selective Electrodes', Sensors and Actuators (1981) 1, 197-260;

Victorova et al, 'New substrates of DNA polymerases', FEBS Let. (1999) 453, 6-10; and Hanazato et al., 'Integrated Multi-Biosensors Based on an Ion-sensitive Field-Effect Transistor Using Photolithographic Techniques', IEEE Transactions on Electron Devices (1989) 36, 1303-1310.

The following example provides fuller details of use of an ISFET sensing apparatus in accordance with the invention to monitor single base primer extension.

EXAMPLE 1

ISFET Monitoring of Single Base Primer Extension

The ISFET output from a reaction where there is an expected single nucleotide base incorporated was monitored and compared to the ISFET output from a non-expected base incorporation signal. A single ISFET with a silver/silver chloride reference electrode was used and the pH change was measured in a very weakly buffered 50 μl reaction volume (FIG. 5). The output of the ISFET was measured using constant charge source-follower instrumentation which monitored pH by keeping the ISFET gate voltage and drain current constant and recording changes in gate-source voltage, corresponding to the pH-dependent change in the ISFET's flat-band voltage.

Single-stranded oligonucleotides (5'-ACATCTGAGTCT-GTAGTCTA-3'; SEQ ID NO:1) were purchased from MWG-Biotech. A 1 nmol/μl of oligonucleotide was annealed with a slight excess of primer (5'-TAGACTAC-3') and 5 μl was added to a reaction mixture containing 1 mM NaCl and 2.5 mM MgCl2.

Figure 14:
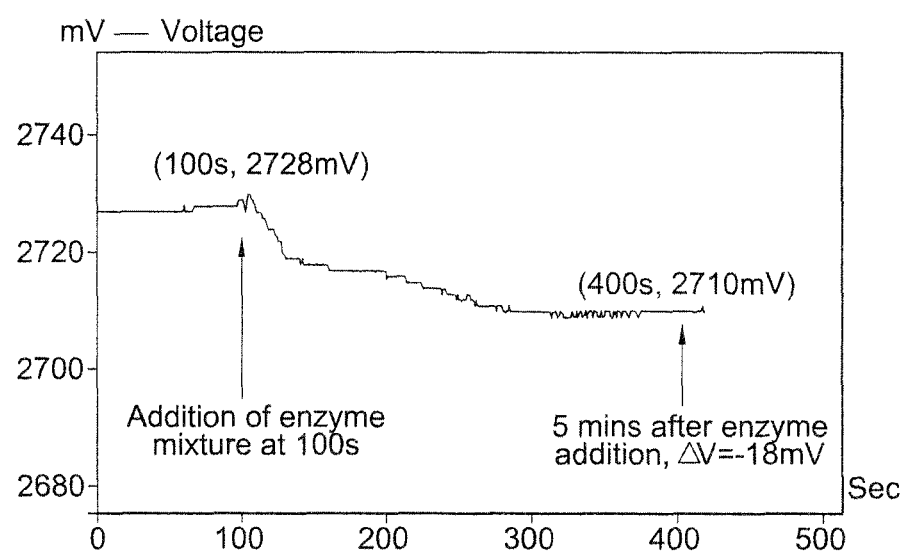
FIG. 14: ISFET reading with provision of complementary dNTP (dATP) for template as described in Example 1.
Figure 15:
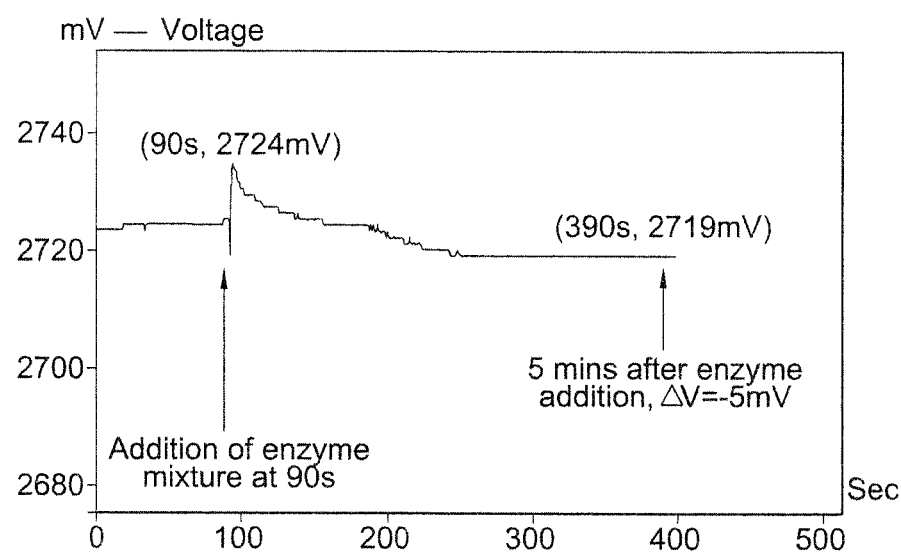
FIG. 15: ISFET reading with provision of non-complementary dNTP (dCTP) for template as described in Example 1.

DNA polymerase (Klenow fragment, 3' exonuclease deficient) was obtained from Amersham Biosciences. 0.5 μl of this Klenow fragment was added to the reaction mixture to produce a final enzyme concentration of 0.1 units/μl. dNTP, which was either complementary (adenosine, FIG. 14) or non-complementary (FIG. 15) for the position on the template oligonucleotide immediately following the 3' end of the hybridised primer, was mixed with the enzyme just prior to its addition and the enzyme/dNTP mixture added to the reaction chamber to trigger an extension reaction. The final dNTP concentration was 1 mM. The start pH of the DNA mixture was adjusted to 7.0 using small quantities of NaOH and HCl. All reactions were conducted at 37.1° C. by placing the ISFET in a thermostated waterbath and the ISFET output was recorded using a commercial 12-bit analogue to digital converter (PICO Technologies Ltd.) connected to a laptop computer.

The above procedure was repeated for all four nucleotides.

It was observed that after the addition of the complementary nucleotide (dATP), ISFET voltage output decreased significantly from baseline steady-state ISFET output (FIG. 14) whereas for addition of non-complementary nucleotides (FIG. 15), the ISFET output signal did deviate, but tended back towards the baseline signal. Therefore, the significantly lower ISFET signal endpoint for complementary nucleotide addition, represented proton release through single nucleotide extension of the hybridised primer on the template oligonucleotide.

Repetition of experiments for both complementary and non-complementary dNTPs showed that deviations from baseline ISFET signal output upon addition of the enzyme/dNTP mixture can occur in either direction, possibly due to adsorption of DNA, agitation, adsorption of Klenow fragment, ISFET signal drift etc. Therefore when using this method to determine which of the four nucleotides added has been involved in chain extension, a differential comparison of all four ISFET outputs is required to eliminate background effects such as these and determine which nucleotide addition has given a significant and steady deviation from baseline.

As a variation of the method above, it will be appreciated that a differential arrangement may be employed with a platinum electrode and two ISFETs, one of which is insensitive to the reaction being monitored. Other possible variations will be immediately apparent to those skilled in the art.

The invention claimed is:

1. A sensing apparatus comprising at least two ion sensitive field effect transistors (ISFET) and at least two sets of reagents;
a first of the transistors exposable to an unknown sample and a first of the sets of reagents, and separated from a second of the transistors exposable to an unknown sample and a second of the sets of reagents, different from the first set of reagents; and
further comprising means for determining the difference between electrical signals generated by the first and second transistors, to provide an output signals to identify the sample.

2. The sensing apparatus according to claim 1, further comprising microfluidic chambers having a volume of less than 50 µL.

3. The sensing apparatus according to claim 2, wherein each ISFET is housed within the microfluidic chamber to receive the unknown sample and one of the sets of reagents.

4. The sensing apparatus according to claim 1, further comprising microchannels to deliver the unknown sample.

5. The sensing apparatus according to claim 4, further comprising a plate covering a silicon chip integrating the ISFETs, the plate having portions removed to provide said microfluidic chambers.

6. The sensing apparatus according to claim 5, further comprising a heating element and a temperature sensor integrated into the silicon chip.

7. The sensing apparatus according to claim 2, further comprising means to deliver the sample to more than one of said microfluidic chambers for simultaneous testing of more than one variation of the sample.

8. The sensing apparatus according to claim 2, further comprising a seal for the microfluidic chambers.

9. The sensing apparatus according to claim 1, wherein the unknown sample comprises a target nucleic acid.

10. The sensing apparatus according to claim 1, wherein the sets of reagents comprise allele specific reagents.

11. The sensing apparatus according to claim 9, wherein the sets of reagents comprise one or more types of nucleotide and an oligonucleotide serving as a primer or probe for the target nucleic acid.

12. The sensing apparatus according to claim 9, wherein one of the sets of reagents is complementary and one of the sets of reagents is non-complementary with the target nucleic acid.

13. The sensing apparatus according to claim 1, wherein each set of reagents comprise magnesium.

14. The sensing apparatus according to claim 1, further comprising beads having probes or primers immobilised on the surface.

15. The sensing apparatus according to claim 1, wherein the apparatus further comprises monitoring means arranged to monitor the time at which fluctuations occur in the electrical signals generated by the first and second transistors and the magnitude of said fluctuations.

16. The sensing apparatus according to claim 1, wherein the first and second transistors are connected to first and second operational amplifiers respectively.

17. The sensing apparatus according to claim 1, wherein the first and second transistors are arranged to form part of first and second operational amplifiers respectively.

18. The sensing apparatus according to claim 1, wherein an electrical signal is passed to an electrode to maintain voltages applied to the first and second transistors at a constant level.

* * * * *